US006325971B1

(12) United States Patent
Hayes

(10) Patent No.: US 6,325,971 B1
(45) Date of Patent: Dec. 4, 2001

(54) METHOD AND SYSTEM FOR DISBURSING OZONE INTO A POULTRY HOUSE

(76) Inventor: Charles Hayes, 3473 Trinity Church Rd., Seagrove, NC (US) 27341

(*) Notice: Subject to any disclaimer, the term of this patent is extended or adjusted under 35 U.S.C. 154(b) by 0 days.

(21) Appl. No.: 08/989,723

(22) Filed: Dec. 12, 1997

(51) Int. Cl.[7] .............................. A01N 2/20; A01K 31/18

(52) U.S. Cl. ............................ 422/32; 119/437; 119/448; 119/534

(58) Field of Search .................................... 422/28, 32, 5, 422/123, 292; 43/125; 119/416, 432, 437, 442, 447, 450, 448, 479, 525, 534, 677; 454/179, 296, 297, 903

(56) References Cited

U.S. PATENT DOCUMENTS 3,110,286 * 11/1963 Clute .
3,918,404 * 11/1975 Bunger .
4,168,799 * 9/1979 Turner .
4,504,011 * 3/1985 Farrell .
5,624,635 4/1997 Pryor ...................................... 422/32
5,666,905 * 9/1997 Mackin et al. ....................... 119/448
5,737,850 * 4/1998 Hendrix ........................... 119/442 X

* cited by examiner

*Primary Examiner*—Elizabeth McKane
(74) *Attorney, Agent, or Firm*—Rhodes, Coates, & Bennett, LLP

(57) ABSTRACT

The present invention relates to a system for disbursing ozone throughout a poultry house in order to disinfect the same and to reduce the concentration of pathogens found within the poultry house. An ozone generator is associated with the poultry house and ozone produced by the generator is directed through a lower main duct that disburses ozone upwardly through litter disposed on the poultry house floor. In addition, the same generator directs the produced ozone through an upper main duct and ozone is disbursed from conduits leading from the upper main duct into the air.

7 Claims, 4 Drawing Sheets

10
46
50
41
42
50
14
14

METHOD AND SYSTEM FOR DISBURSING OZONE INTO A POULTRY HOUSE

FIELD OF THE INVENTION

The present invention relates to poultry houses and to processes for reducing the concentration of pathogens therein, and more particularly to a system and process for dispersing ozone within a poultry house for the purpose of reducing pathogen concentrations within the poultry house.

BACKGROUND OF INVENTION

As the United States poultry industry has grown and matured over the past twenty years, poultry prices have tended to remain relatively stable. Given that the cost of ancillary goods and services associated with poultry production has continuously escalated over the same period, the relative stability of poultry prices indicates that there has been and continues to be constant pressure to develop new technology and production methodologies aimed at reducing production costs by way of increasing overall production efficiency.

Two areas of particular interest to commercial poultry producers, with regard to their stock, are feed conversion ratios and bird mortality rates. Feed conversion ratio relates the amount of feed consumed by a bird to produce a pound of product, and bird mortality rates relate to the premature death and hence, complete loss of the intended final product. Those skilled in the art will appreciate that commercial producers strive to maximize feed conversion ratios, and minimize bird mortality rates, as optimizing either of these parameters would ultimately lead to lower overall production costs and hence greater profit margins.

One major factor relevant to both the aspects of feed conversion ratios and bird mortality rates, is the ambient pathogen concentration within the poultry house environment. It has been well documented, through extensive research, that higher ambient pathogen levels generally lead to less than optimal feed conversion ratios, while leading to higher than optimal mortality rates. Therefor, it is reasonable to assume that generally lowering ambient pathogen concentrations within the poultry house would lead to improvements in both the feed conversion ratios and mortality rates, and hence from the discussion above, lead to a generally more cost efficient operation. These are the primary motivating factors behind the development and disclosure of the present invention presented herein.

DETAILED DESCRIPTION OF THE INVENTION

Figure 2:
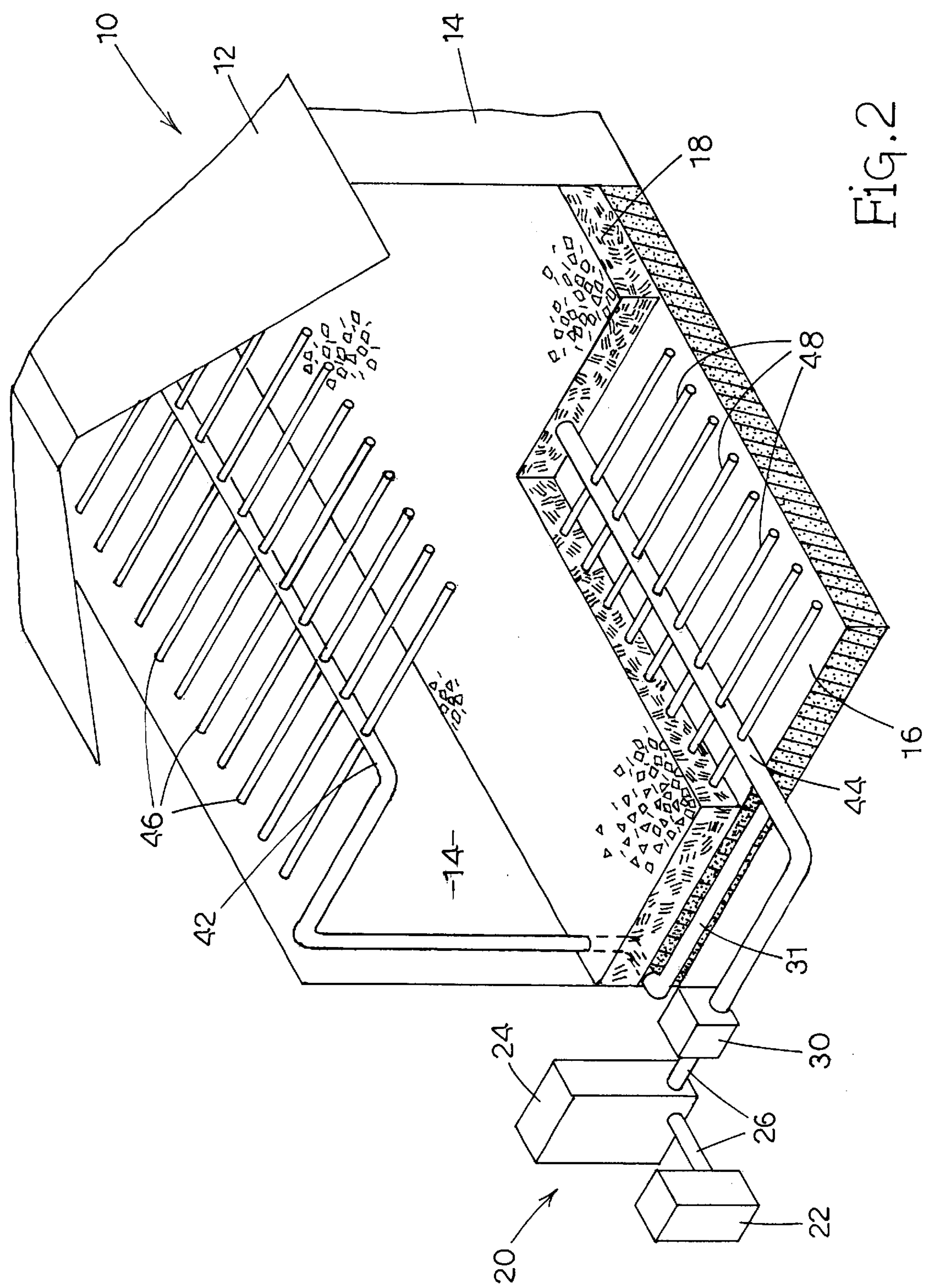
FIG. 2 is a fragmentary, perspective view of a typical poultry house showing the ozone dispersion system of the present invention incorporated therein.
Figure 3:
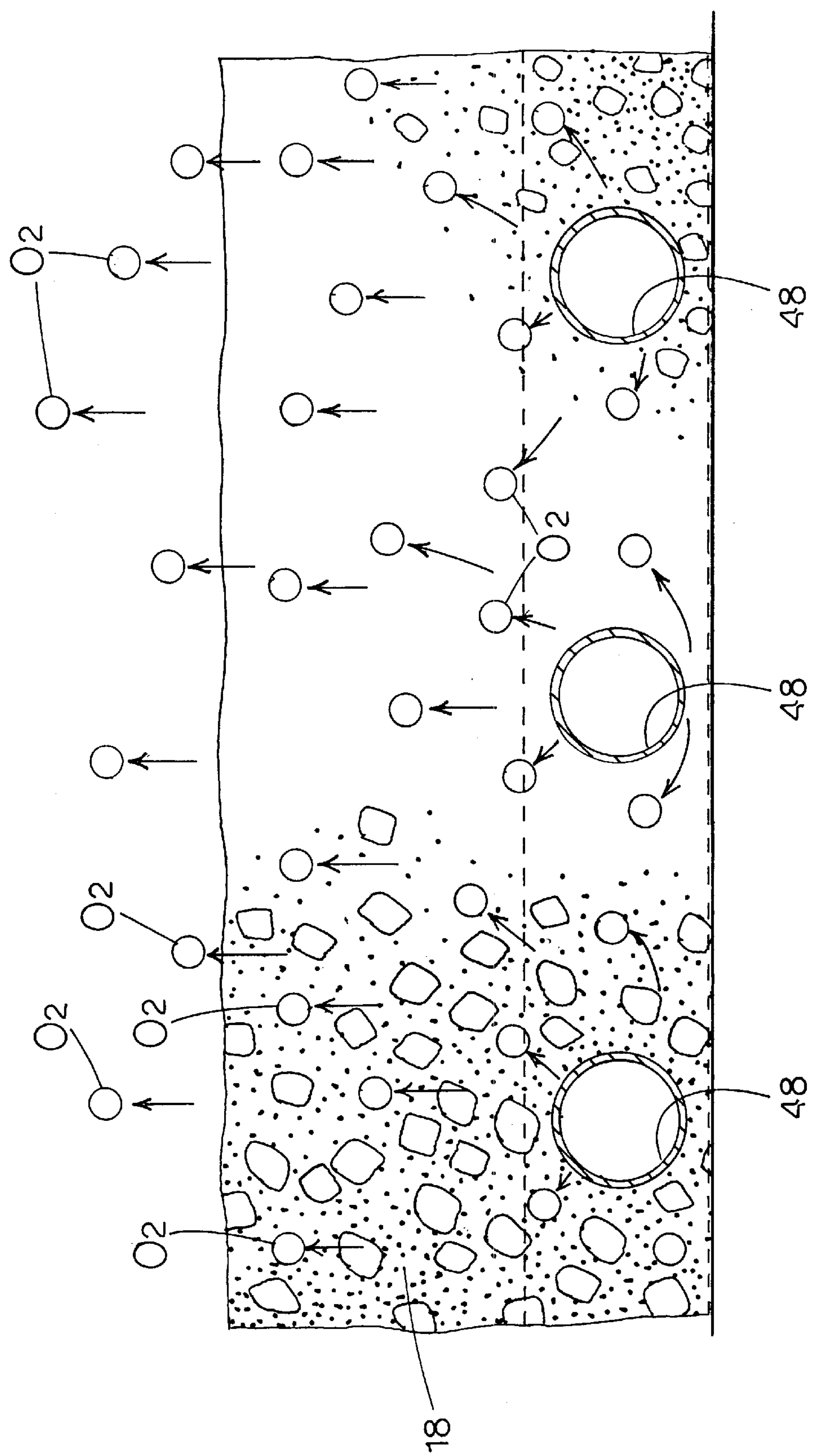
FIG. 3 is a transverse, sectional view through the bed of poultry litter and the underlying floor, illustrating the ozone dispersion conduits and the dispersion of ozone into and through the poultry litter.
Figure 4:
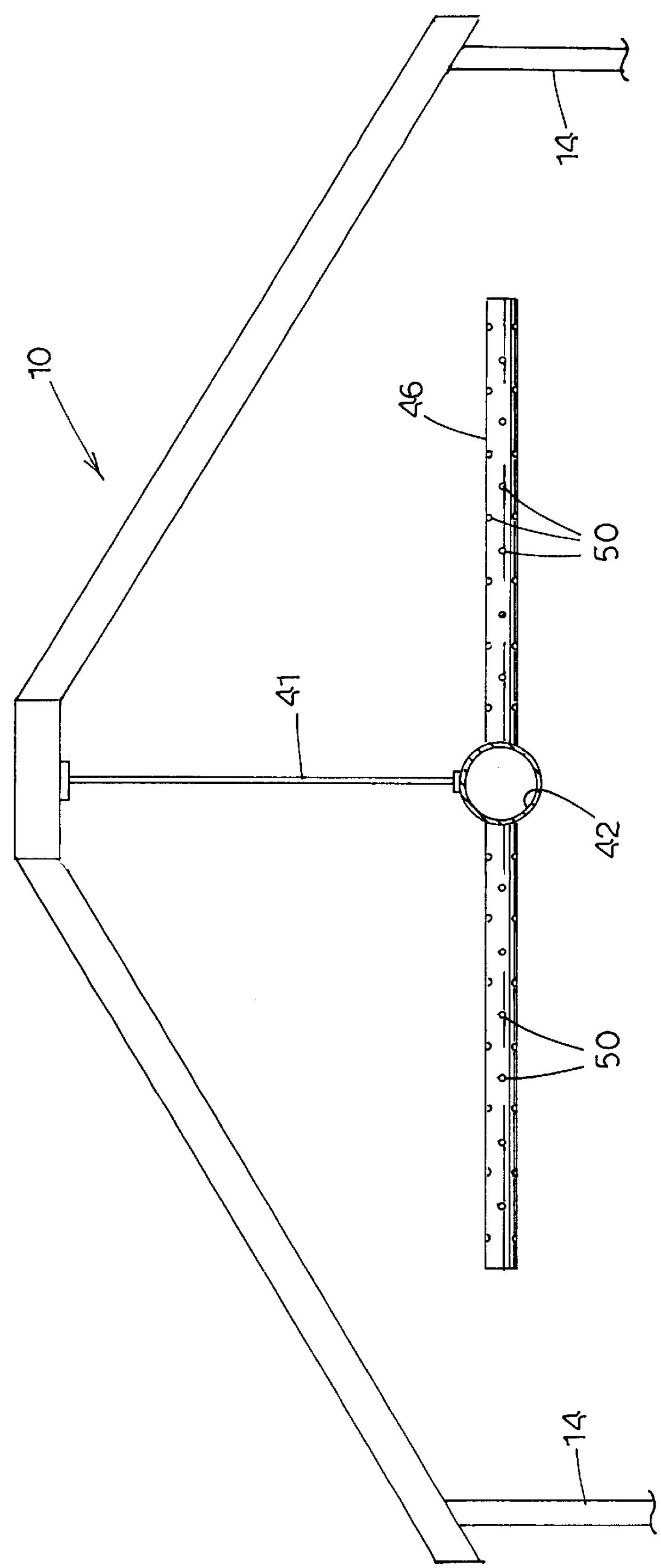
FIG. 4 is a sectional view of the overhead ozone diffusion assembly that forms a part of the present invention.

The present invention entails a method for pathogen concentration reduction in a poultry house utilizing ozone. A typical ozone equipped poultry house 10 is shown in FIGS. 2–4. The house 10 is comprised generally of a roof 12, a plurality of walls 14, a floor 16, and a bed of litter material 18 disposed on top of the floor. While poultry house floors 16 are typically comprised of dirt, it will be appreciated by those skilled in the art that other structurally suitable materials such as concrete, wood or composites could be utilized. The layer of material that covers the floor 16 and forms the litter bed 18 typically consists of wood shavings, although other alternate materials, such as spent peanut hulls, can be employed. With use, poultry excrements become intermixed in the litter bed 18 material, serving to encourage the growth and sustain the presence of potentially harmful pathogens.

Located outside or inside of the house 10 is an ozone generation system 20 comprising an oxygen source 22 and an ozone reactor 24 which generates a stream of ozone gas. Transfer ducts 26 direct oxygen to, and ozone from, the generation system 20. The details of the ozone generation system 20 are not dealt with herein because such is not relevant per se to the present invention and, in addition, ozone generators are appreciated by those ordinarily skilled in the art. The ozone generation system 20 which is referred to herein is intended to be a conventional and commercially available system by design. Particularly, ozone generators of the type contemplated by the present invention are manufactured and sold by $TR10_3$ Industries, Inc. of Fort Pearce, Fla. In addition, one is referred to U.S. Pat. No. 5,514,345 which discloses an ozone generating system for providing ozone that disinfects an enclosed area. This patent and its disclosure are expressly incorporated by reference.

Disposed in series with the ozone generation system 20 is a blower unit 30, the output of which is divided between a main overhead duct 42 and a main litter bed duct 44. In the design shown in FIG. 2, there is provided a lateral connector conduit 31 that turns and extends upwardly along the wall 14 of the poultry house and makes a final turn and joins the main overhead duct 42. The main overhead duct 42 is suspended by hangers 41 and disposed generally centrally beneath the roof 12 and above the litter bed 18. A plurality of overhead diffuser conduits 46 extend radially outward from the central axis of the main duct 42. As illustrated in FIGS. 2 and 4, the overhead diffuser conduits are generally longitudinally spaced along the main overhead duct 42 and extend outward from opposite sides. As with the main overhead duct 42, the diffuser conduits 46 are also disposed beneath the roof 12 and generally above the litter bed 18.

The main litter bed duct 44 is disposed adjacent the floor 16 and litter bed 18, and extends generally centrally down the poultry house as shown in FIG. 2. A plurality of litter bed diffuser conduits 48 extend radially outward from the central axis of the main duct 44. As illustrated in FIGS. 2 and 3, the litter bed diffuser conduits 48 are generally longitudinally spaced along the main litter bed duct 44 and extend outward from opposite sides. As with the main litter bed duct 44, the diffuser conduits 48 are also disposed adjacent the floor 16 and generally under the litter bed.

Figure 1:
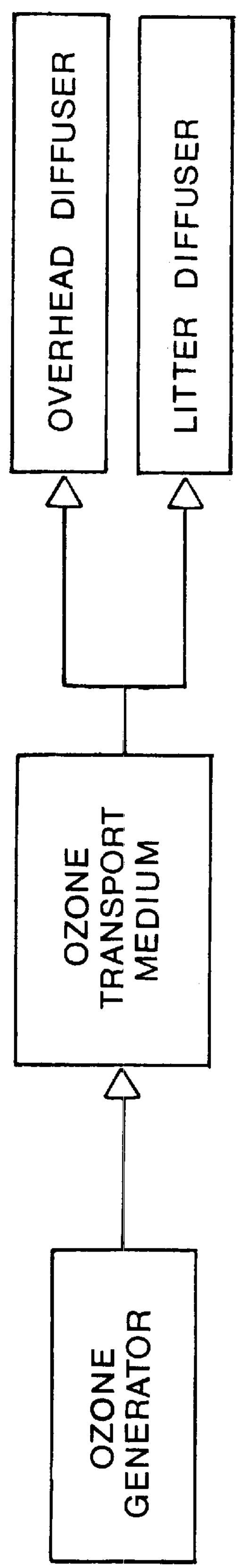
FIG. 1 is a schematic diagram depicting the basic components of the ozone dispersion system of the present invention.

As shown in the functional schematic diagram of FIG. 1, operation of the present invention involves the generation of an ozone gas stream, the transport and distribution of the gas stream, and the release of the gas stream via the overhead and litter bed based diffuser components. The ozone reactor 24 receives an input stream of oxygen from the oxygen source 22 and produces, through a chemical reaction process not detailed herein, an output stream of ozone gas. The blower unit 30 effectively pumps the ozone gas stream from the generator system 20 to the duct delivery system.

The duct system branches into the main overhead duct 42 and the main litter bed duct 44. The main overhead duct 42 distributes a component of the ozone gas stream to the plurality of overhead diffuser conduits 46, as shown in FIGS. 2 and 4. The ozone gas stream flows through the diffuser conduits 46 and is dispersed directly into the poultry house 10 atmosphere via the perforations 50 disposed in the overhead diffuser conduits. As illustrated in FIG. 2, the main litter bed duct 44 distributes a component of the ozone gas stream to the plurality of litter bed diffuser conduits 48. The ozone gas stream flows through the sub-surface diffuser conduits 48 and is released into the surrounding litter bed material 18 via perforations (not shown) disposed in the litter bed diffuser conduits 48. 3 and 4. Under pressure provided by the blower unit 30, ozone is dispersed from the diffuser conduits 48 directly into the litter material 18, and over time, percolates through the litter material towards the atmosphere above the litter bed 18. See FIG. 3 where the ozone being disbursed through the litter 18 is graphically illustrated by the reference $\mathbf{0}_2$. During the percolation interval, the ozone is in intimate contact with the litter bed material, and consequently the pathogens contained therein. By controlling the concentration and rate of dispersion of the ozone gas stream within the litter bed 18, ozone exposure levels that are lethal to pathogens living within the litter bed material can be maintained indefinitely. Upon reaching the top surface of the litter bed 18, the ozone gas further diffuses into the atmosphere above the litter bed, joining the ozone that has been dispersed directly from the overhead diffuser conduits 46.

The system and method described herein provides a means of introducing and effectively dispersing ozone throughout both the poultry house atmosphere and litter bed material for the purpose of pathogen reduction. The system and process shown in the drawing and described herein is considered to be an effective approach to reducing the concentration of pathogens within a poultry house environment. However, it will be appreciated by those skilled in the art that other specific designs can be utilized for disbursing ozone through the litter of a poultry house and into the air found within the confines of the poultry house.

It will be appreciated that the system of the present invention could be designed so as to dispense ozone in certain zones within the poultry house. As a part of this approach, there would be a control system for enabling selected zones to be sequentially treated. This would, of course, reduce the overall cost of the ozone generator and would make the entire system more cost-effective.

The present invention may, of course, be carried out in other specific ways than those herein set forth without parting from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A method, utilizing ozone, for reducing pathogen concentrations in a poultry house environment comprising:

a) generating ozone;

b) directing the generated ozone underneath a bed of litter disposed in the poultry house; and c) diffusing the ozone through the litter for the purpose of reducing pathogen concentrations within the litter bed.

2. The method of claim 1 wherein delivery of the ozone to the litter bed is accomplished via a plurality of ozone conduits which are disposed beneath the litter bed.

3. The method of claim 2 wherein ozone is diffused through the litter bed from a plurality of perforations formed in the conduits.

4. The method of claim 2 wherein the ozone conduits are formed of a flexible, pliable material so as to permit coiling of the conduit and also allows for conformation to a wide variety of litter bed geometries.

5. The method of claim 1, further including diffusing the generated ozone directly into the airspace within the poultry house.

6. The method of claim 5 wherein the delivery of the ozone into the airspace of the poultry house is accomplished via a plurality of ozone conduits which are disposed generally between a roof that forms a part of the poultry house and the bed of litter.

7. The method of claim 6 wherein the conduits disposed between the roof and the bed of litter include multiple perforations for diffusing ozone from the conduit.

* * * * *